(12) United States Patent
Ahner et al.

(10) Patent No.: US 9,217,715 B2
(45) Date of Patent: Dec. 22, 2015

(54) APPARATUSES AND METHODS FOR MAGNETIC FEATURES OF ARTICLES

(71) Applicant: SEAGATE TECHNOLOGY LLC, Cupertino, CA (US)

(72) Inventors: Joachim Walter Ahner, Livermore, CA (US); David M. Tung, Livermore, CA (US); Stephen Keith McLaurin, Sunnyvale, CA (US)

(73) Assignee: Seagate Technology LLC, Cupertino, CA (US)

( * ) Notice: Subject to any disclaimer, the term of this patent is extended or adjusted under 35 U.S.C. 154(b) by 0 days.

(21) Appl. No.: 14/193,808

(22) Filed: Feb. 28, 2014

(65) Prior Publication Data

US 2014/0354982 A1 Dec. 4, 2014

Related U.S. Application Data

(60) Provisional application No. 61/829,160, filed on May 30, 2013.

(51) Int. Cl.
*G01N 21/00* (2006.01)
*G01N 21/95* (2006.01)
*G01N 21/47* (2006.01)

(52) U.S. Cl.
CPC ............ *G01N 21/95* (2013.01); *G01N 21/4738* (2013.01)

(58) Field of Classification Search
CPC ... G01N 21/4738; G01N 21/95; G01N 21/94; G01N 27/82; G01R 33/12
USPC .............. 356/237.1–237.5; 369/53.15, 53.17, 369/53.22, 53.41; 250/559.14, 559.41
See application file for complete search history.

(56) References Cited

U.S. PATENT DOCUMENTS

| | | | |
|---|---|---|---|
| 4,207,467 A | 6/1980 | Doyle | |
| 4,477,890 A | 10/1984 | Ceshkovsky et al. | |
| 4,551,919 A | 11/1985 | Sakata et al. | |
| 4,598,997 A | 7/1986 | Auderset et al. | |
| 4,618,773 A | 10/1986 | Drukier | |
| 4,794,550 A | 12/1988 | Greivenkamp | |
| 4,806,776 A | 2/1989 | Kley | |
| 4,975,571 A | 12/1990 | McMurtry et al. | |
| 5,058,178 A | 10/1991 | Ray | |
| 5,066,130 A | 11/1991 | Tsukiji et al. | |

(Continued)

FOREIGN PATENT DOCUMENTS

| | | |
|---|---|---|
| JP | 06-241758 A | 9/1994 |
| JP | 08-075661 A | 3/1996 |

(Continued)

OTHER PUBLICATIONS

Candela CS10, Optical X-BeamTM Surface Analyzer, Product Description (www.klatencor.com/defect-inspection/candela-cs10.html), accessed Apr. 17, 2013.

(Continued)

*Primary Examiner* — Hoa Pham

(57) ABSTRACT

Provided herein are apparatuses and methods related thereto, wherein at least one apparatus includes: a photon emitting means configured to emit photons, wherein the photons are scattered from magnetic features of an article; a photon detector array configured to receive scattered photons; and a processing means configured to differentiate the magnetic features from the scattered photons.

21 Claims, 11 Drawing Sheets

(56) References Cited

U.S. PATENT DOCUMENTS

Figure 1:
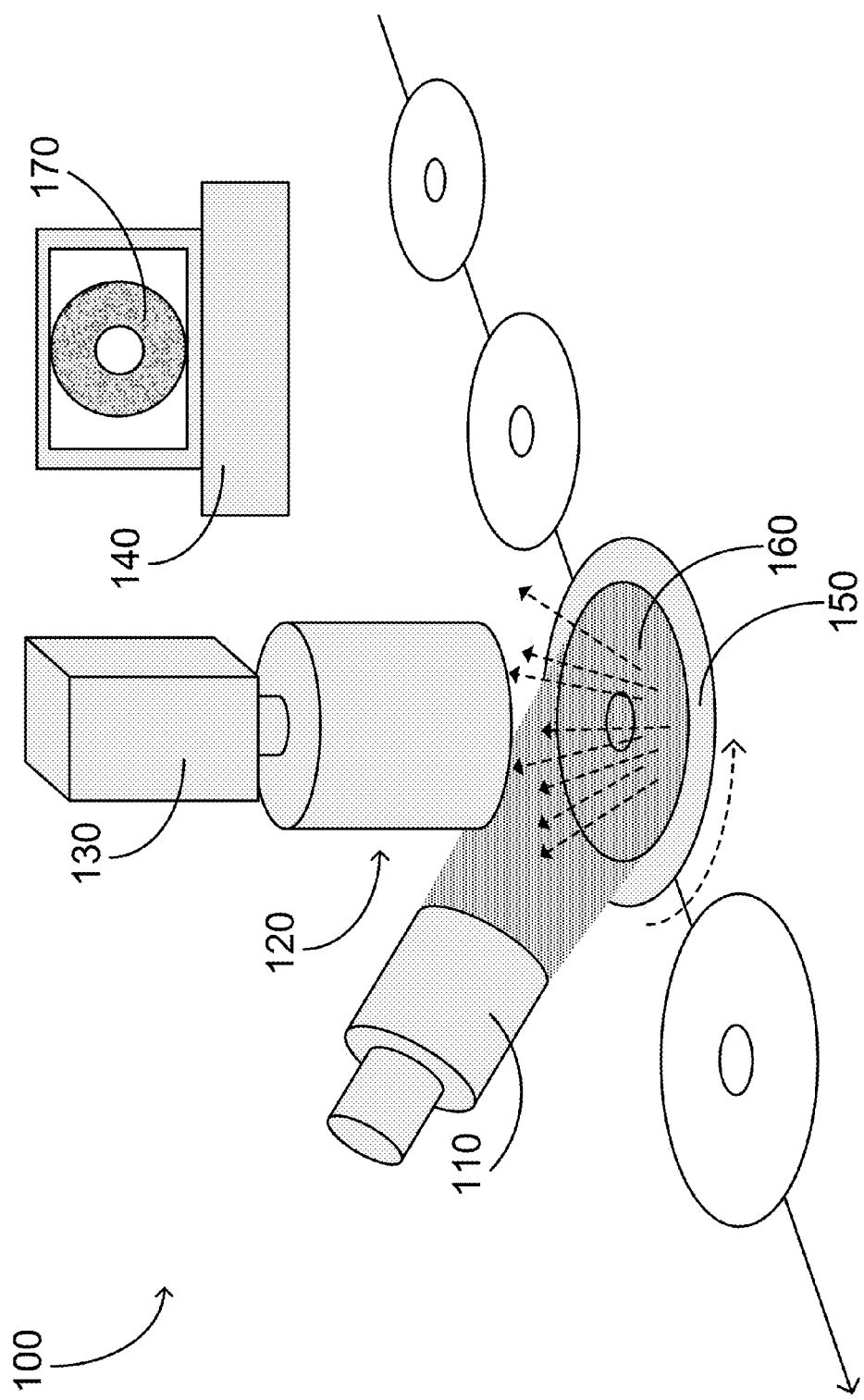

| | | | |
|---|---|---|---|
| 5,131,755 | A | 7/1992 | Chadwick et al. |
| 5,168,322 | A | 12/1992 | Clarke et al. |
| 5,455,870 | A | 10/1995 | Sepai et al. |
| 5,610,392 | A | 3/1997 | Nagayama et al. |
| 5,627,638 | A | 5/1997 | Vokhmin |
| 5,661,559 | A | 8/1997 | Brezoczky et al. |
| 5,726,455 | A * | 3/1998 | Vurens ............... 250/559.28 |
| 5,737,072 | A | 4/1998 | Emery et al. |
| 5,774,212 | A | 6/1998 | Corby, Jr. |
| 5,778,039 | A | 7/1998 | Hossain et al. |
| 5,781,649 | A * | 7/1998 | Brezoczky ............... 382/108 |
| 5,859,698 | A | 1/1999 | Chau et al. |
| 5,898,491 | A | 4/1999 | Horai et al. |
| 5,933,236 | A | 8/1999 | Sommargren |
| 5,973,839 | A | 10/1999 | Dorsel |
| 6,256,097 | B1 | 7/2001 | Wagner |
| 6,392,745 | B1 | 5/2002 | Mavliev et al. |
| 6,449,036 | B1 | 9/2002 | Wollmann et al. |
| 6,476,908 | B1 | 11/2002 | Watson |
| 6,483,584 | B1 | 11/2002 | Lee et al. |
| 6,509,966 | B2 | 1/2003 | Ishiguro |
| 6,515,742 | B1 | 2/2003 | Ruprecht |
| 6,529,270 | B1 * | 3/2003 | Bills ..................... 356/237.2 |
| 6,542,248 | B1 | 4/2003 | Schwarz |
| 6,556,783 | B1 | 4/2003 | Gelphman |
| 6,559,458 | B2 | 5/2003 | Rinn |
| 6,559,926 | B2 | 5/2003 | Yamaguchi et al. |
| 6,617,087 | B1 | 9/2003 | Rangarajan et al. |
| 6,617,603 | B2 | 9/2003 | Ishiguro et al. |
| 6,809,809 | B2 | 10/2004 | Kinney et al. |
| 6,819,423 | B2 | 11/2004 | Stehle et al. |
| 6,822,734 | B1 | 11/2004 | Eidelman et al. |
| 6,847,907 | B1 | 1/2005 | Novotny |
| 7,207,862 | B2 | 4/2007 | Nabeya et al. |
| 7,433,031 | B2 | 10/2008 | Xu et al. |
| 7,474,410 | B2 | 1/2009 | Moon |
| 7,489,399 | B1 | 2/2009 | Lee |
| 7,684,057 | B2 | 3/2010 | Sakai |
| 7,751,609 | B1 | 7/2010 | Berman |
| 7,777,876 | B2 * | 8/2010 | Horai et al. ............... 356/237.3 |
| 7,969,567 | B2 | 6/2011 | Yoshida et al. |
| 8,018,585 | B2 | 9/2011 | Hariyama |
| 8,077,305 | B2 | 12/2011 | Owen et al. |
| 8,139,232 | B2 | 3/2012 | Wolf et al. |
| 8,223,326 | B2 | 7/2012 | Kim et al. |
| 8,294,890 | B2 | 10/2012 | Usuda |
| 8,547,545 | B2 | 10/2013 | Sasazawa et al. |
| 2001/0036588 | A1 | 11/2001 | Buschbeck et al. |
| 2002/0088952 | A1 | 7/2002 | Rao et al. |
| 2004/0207836 | A1 | 10/2004 | Chhibber et al. |
| 2004/0231177 | A1 | 11/2004 | Mies |
| 2005/0067740 | A1 | 3/2005 | Haubensak |
| 2005/0099204 | A1 | 5/2005 | Uh et al. |
| 2005/0174575 | A1 | 8/2005 | Norton et al. |
| 2005/0280808 | A1 | 12/2005 | Backhauss et al. |
| 2006/0126062 | A1 | 6/2006 | Tuschel |
| 2006/0147814 | A1 | 7/2006 | Liang |
| 2006/0181700 | A1 * | 8/2006 | Andrews et al. ........... 356/237.2 |
| 2007/0229852 | A1 | 10/2007 | Wack et al. |
| 2008/0174771 | A1 * | 7/2008 | Yan et al. ................. 356/237.5 |
| 2008/0191137 | A1 | 8/2008 | Poteet et al. |
| 2008/0309927 | A1 | 12/2008 | Grueneberg |
| 2009/0009753 | A1 | 1/2009 | Horai et al. |
| 2009/0122304 | A1 | 5/2009 | Jin et al. |
| 2009/0320051 | A1 | 12/2009 | Meerwald et al. |
| 2009/0323051 | A1 | 12/2009 | Matsui |
| 2010/0053602 | A1 * | 3/2010 | Hayashi et al. ............. 356/237.3 |
| 2010/0053603 | A1 * | 3/2010 | Sakaguchi et al. ......... 356/237.4 |
| 2010/0091272 | A1 | 4/2010 | Asada et al. |
| 2011/0066382 | A1 | 3/2011 | Adams |
| 2011/0141272 | A1 | 6/2011 | Uto et al. |
| 2012/0140211 | A1 | 6/2012 | Oshima et al. |
| 2012/0194808 | A1 | 8/2012 | Oka et al. |
| 2013/0077159 | A1 | 3/2013 | Tani et al. |
| 2013/0198697 | A1 | 8/2013 | Hotzel et al. |
| 2013/0301040 | A1 | 11/2013 | Ahner et al, |
| 2014/0043621 | A1 | 2/2014 | Ahner et al. |
| 2014/0098364 | A1 * | 4/2014 | Ahner et al. ............... 356/237.2 |
| 2014/0098368 | A1 | 4/2014 | Ahner,et al. |
| 2014/0104604 | A1 * | 4/2014 | Ahner et al. ............... 356/237.4 |
| 2014/0129179 | A1 | 5/2014 | Xu et al. |
| 2014/0160481 | A1 | 6/2014 | Ahner et al. |
| 2014/0312894 | A1 * | 10/2014 | Bartos et al. ................. 324/252 |
| 2014/0354980 | A1 * | 12/2014 | Tung et al. ................. 356/237.2 |
| 2014/0354981 | A1 * | 12/2014 | Ahner et al. ............... 356/237.2 |
| 2014/0354984 | A1 * | 12/2014 | Tung et al. ................. 356/237.5 |
| 2014/0354994 | A1 | 12/2014 | Ahner et al. |

FOREIGN PATENT DOCUMENTS

| | | |
|---|---|---|
| JP | 08-178867 A | 7/1996 |
| JP | 2003-202214 | 7/2003 |
| JP | 3692685 B2 | 9/2005 |
| JP | 2006-30851 A | 11/2009 |
| JP | 2011-163872 A | 8/2011 |
| JP | 2012-026862 A | 2/2012 |
| JP | 2012-185121 A | 9/2012 |
| KR | 10-0763942 B1 | 10/2007 |
| KR | 10-2011-0021304 A | 3/2011 |
| WO | 96-05503 A1 | 2/1996 |

OTHER PUBLICATIONS

Candela CS20, Advanced Inspection for Compound Semiconductor and Optoelectronic Materials, Optical Surface Analyzer, KLA-Tencor Corporation, 2010.

High-sensitivity, High-speed Dark-field Wafer-defect Inspection System—IS3000, Hitachi Review vol. 55, No. 2, pp. 73-77, Hitachi Ltd., 2006.

Hitachi High-Technologies I-5320 /I-6300—Electron Beam Wafer Inspection System, (www.etesters.com/listing/ea101bfb-1422-08df-aaae-08c275a8ee86/I-5320__~_I-6300_-_Electron_Beam_Wafer_Inspection_System), accessed Jun. 19, 2013.

Hitachi High-Technologies IS3000—Dark Field Wafer Defect Inspection System, (www.etesters.com/listing/ea1312b5-1422-08df-aa4b-5fea5982b63b/IS3000_-_Dark_Field_Wafer_Defect_Inspection_System), accessed Jun. 19, 2013.

Hitachi High-Technologies LS6800—Wafer Surface Inspection System, (www.etesters.com/listing/ea1133d4-1422-08df-aad9-258baeaf6c16/LS6800_-_Wafer_Surfce_Inspection_System), accessed Jun. 19, 2103.

LS Unpatterned Wafer Inspection System, (hitachi-htc.ca/products/semiconductor-metrology-equipment/inspections-systems/wafer-inspection-system/Is-unpatterne), accessed Jun. 19, 2013.

* cited by examiner

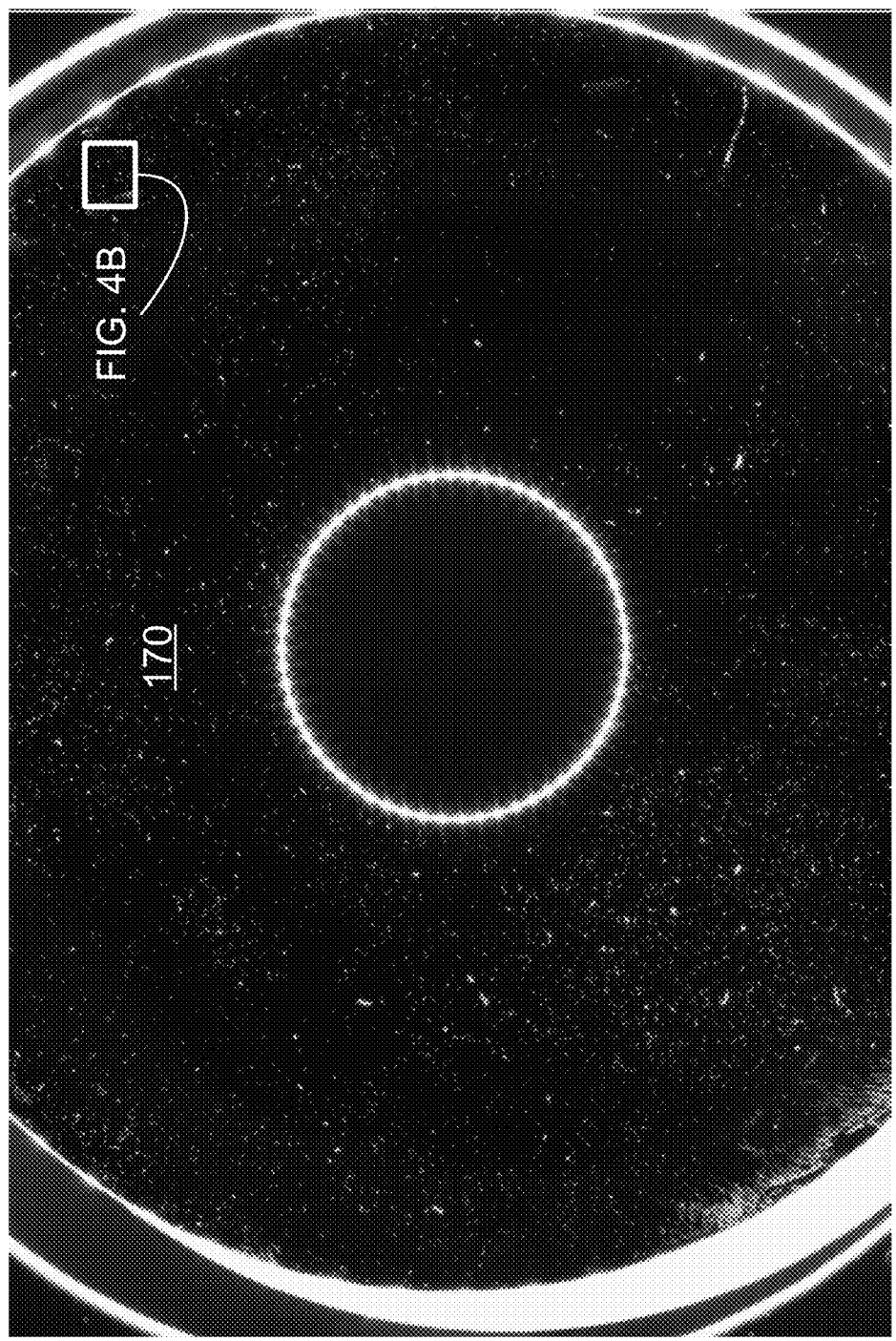

APPARATUSES AND METHODS FOR MAGNETIC FEATURES OF ARTICLES

CROSS REFERENCE

This application claims the benefit of U.S. Provisional Patent Application No. 61/829,160, filed May 30, 2013.

BACKGROUND

An article may be inspected for features, including defects that might degrade the performance of the article or a system including the article. For example, a hard disk for a hard disk drive may be fabricated on a production line and inspected for defects that might degrade the performance of the disk or the hard disk drive. Accordingly, apparatuses and methods may be used to inspect articles for features.

SUMMARY

Provided herein are apparatuses and methods related thereto, wherein at least one apparatus includes: a photon emitting means configured to emit photons, wherein the photons are scattered from magnetic features of an article; a photon detector array configured to receive scattered photons; and a processing means configured to differentiate the magnetic features from the scattered photons.

These and other features and aspects of the concepts provided herein may be better understood with reference to the following drawings, description, and appended claims.

DRAWINGS

FIG. 1 provides a schematic illustrating detection of features of articles according to one or more aspects.

Figure 2A:
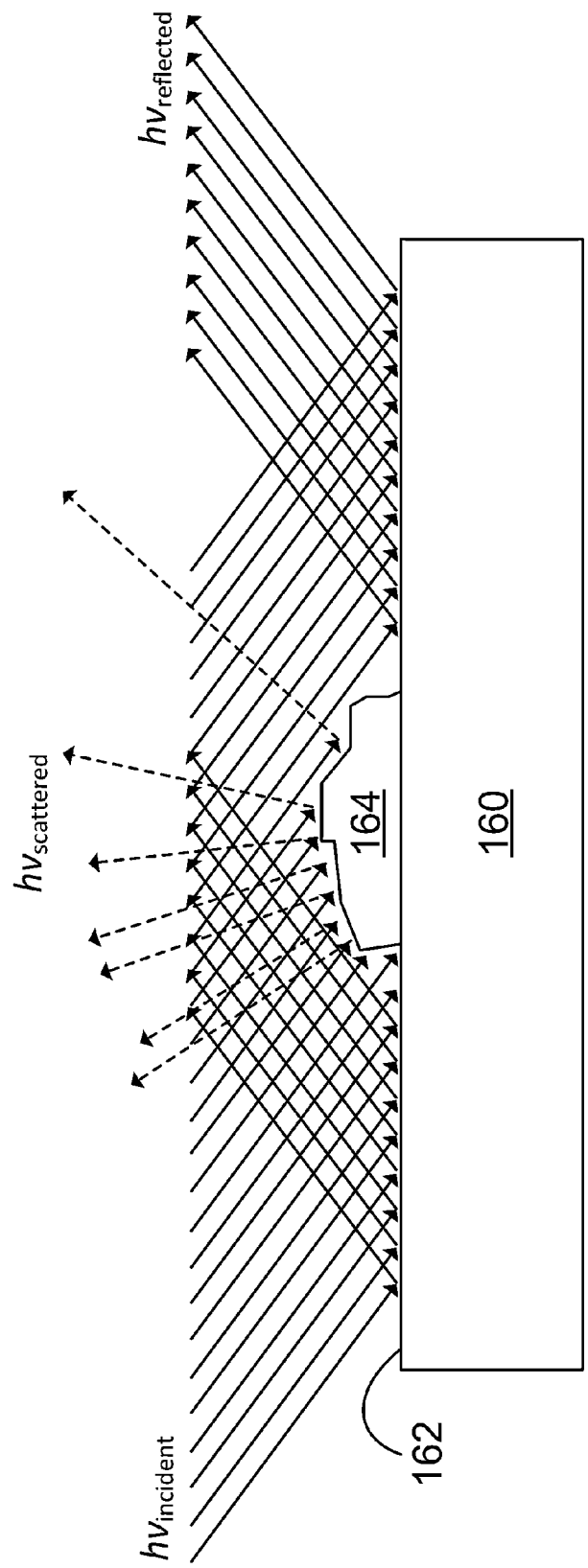

FIG. 2A provides a schematic illustrating photon scattering from a surface feature of an article according to one or more aspects.

Figure 2B:
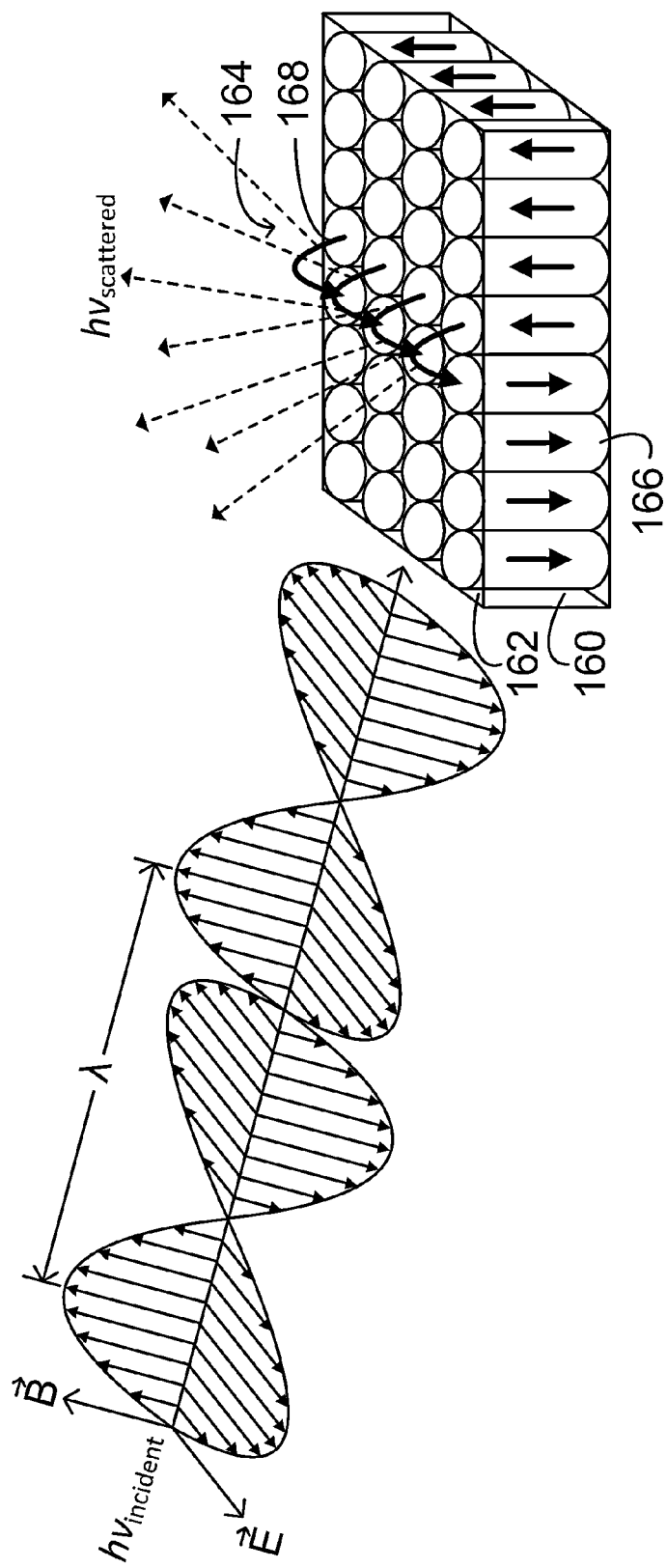

FIG. 2B provides a schematic illustrating photon scattering from a magnetic feature of a portion of an article according to one or more aspects.

Figure 3:
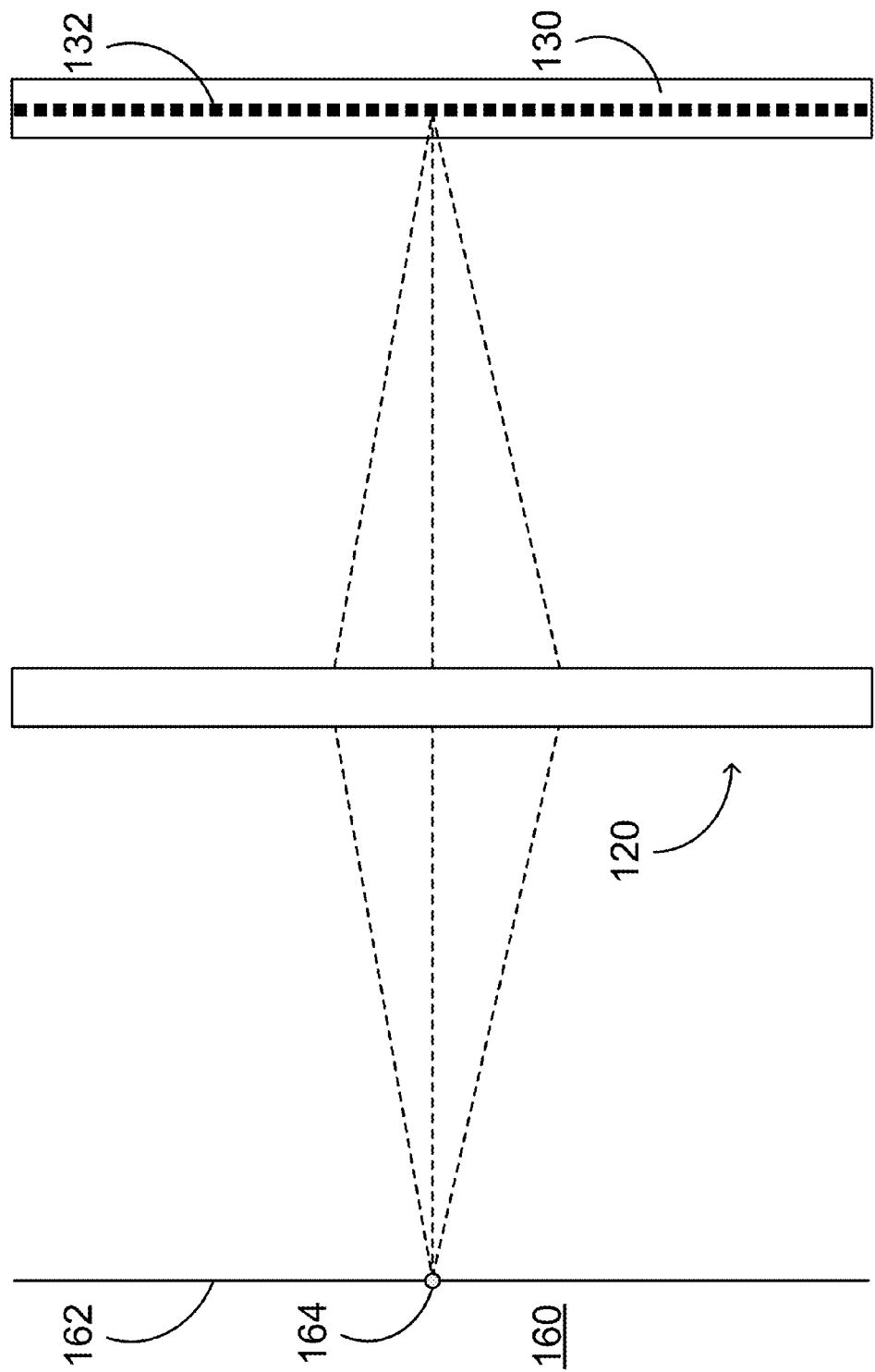

FIG. 3 provides a schematic illustrating photons scattering from a surface feature of an article, through an optical component, and onto a photon detector array according to one or more aspects.

FIG. 4A provides an image of a surface features map of an article according to one or more aspects.

Figure 4B:
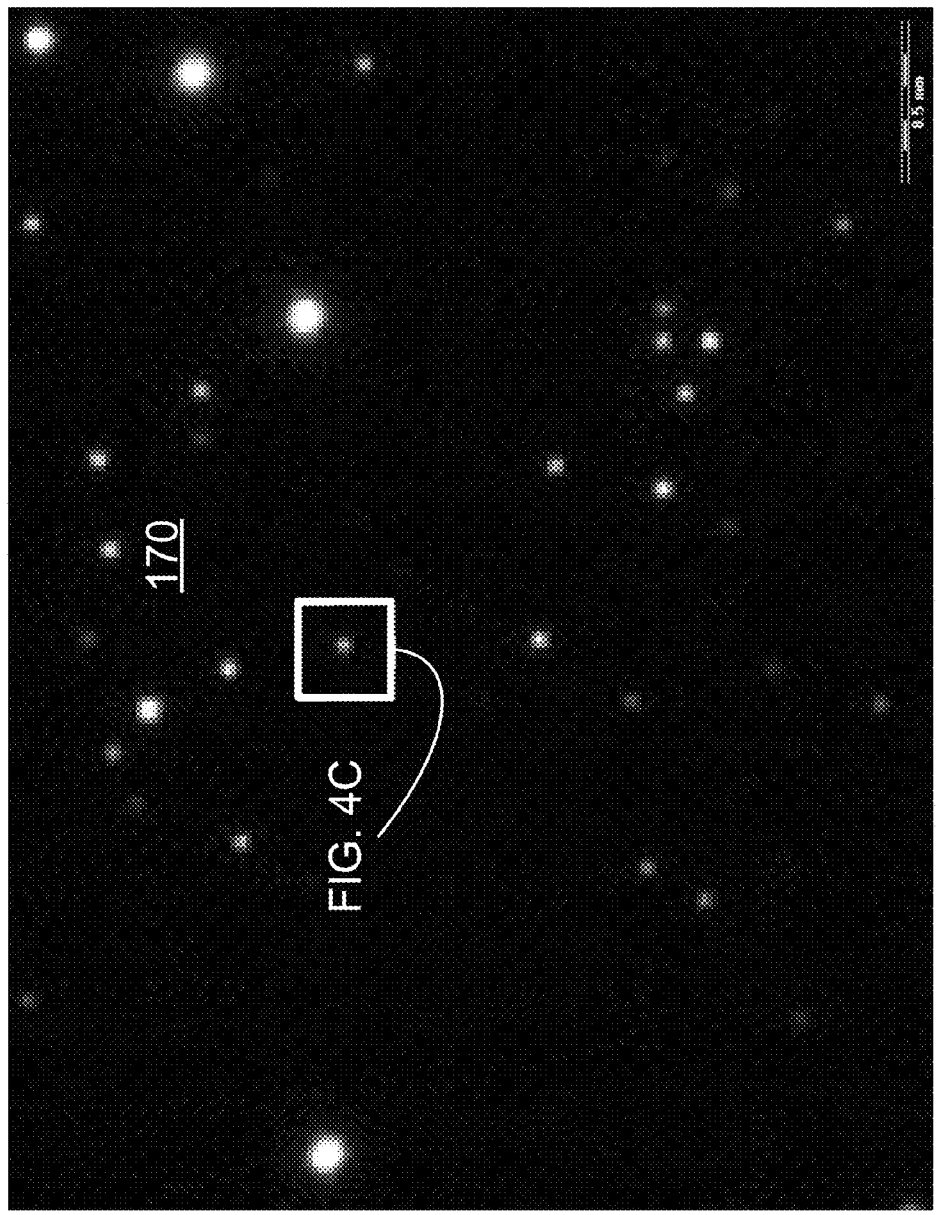

FIG. 4B provides a close-up image of a surface features map of an article according to one or more aspects.

Figure 4D:
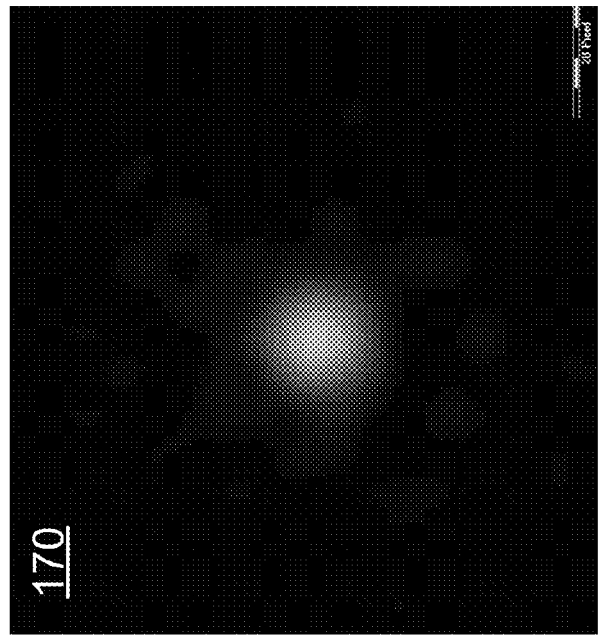
Figure 4C:
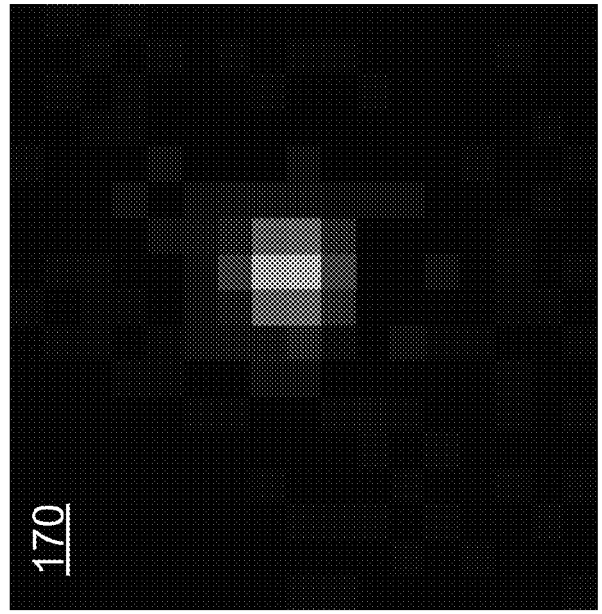

FIG. 4C (top) provides a close-up image of a surface feature of a surface features map, and FIG. 4C (bottom) provides a photon scattering intensity distribution of the surface feature, according to one or more aspects.

FIG. 4D (top) provides a close-up, pixel-interpolated image of a surface feature of a surface features map, and FIG. 4D (bottom) provides a photon scattering intensity distribution of the pixel-interpolated surface feature, according to one or more aspects.

Figure 5A:
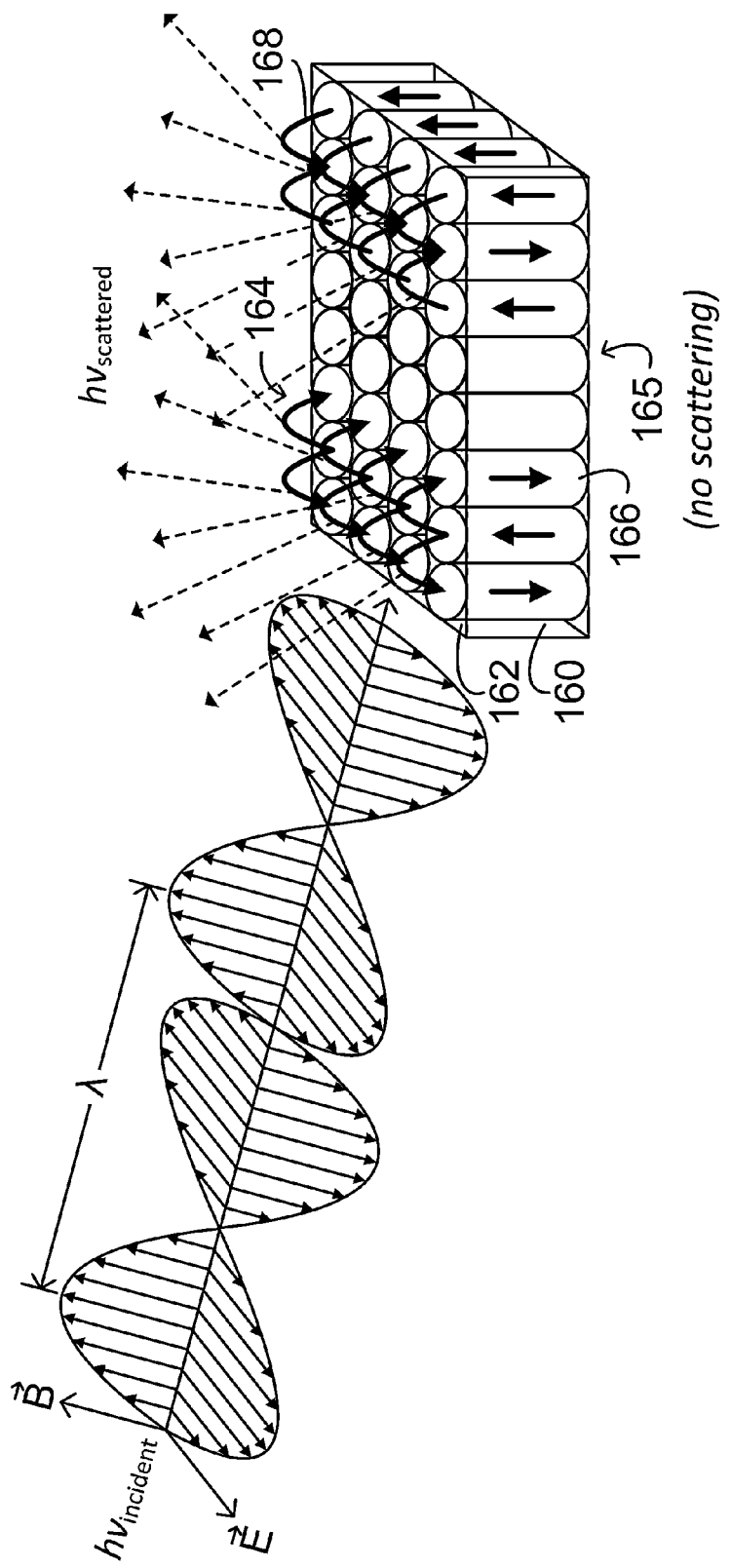

FIG. 5A provides a schematic illustrating a lack of photon scattering from a magnetic anomaly of a portion of an article according to one or more aspects.

Figure 5B:

FIG. 5B provides an image of a magnetic features map of an article according to one or more aspects.

Figure 5C:
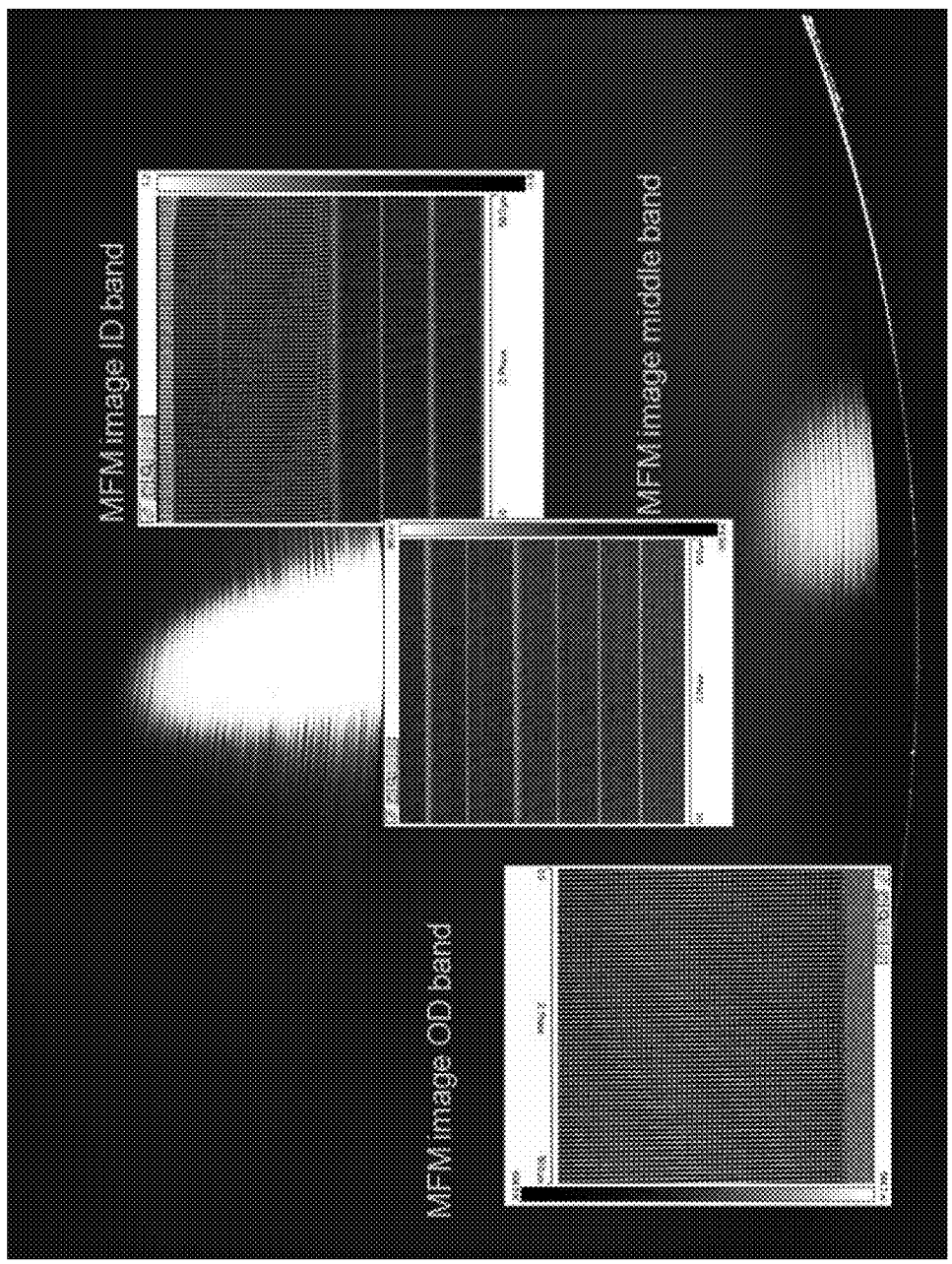

FIG. 5C provides an image of a magnetic features map and magnetic force microscopy images of an article according to one or more aspects.

Figure 6:
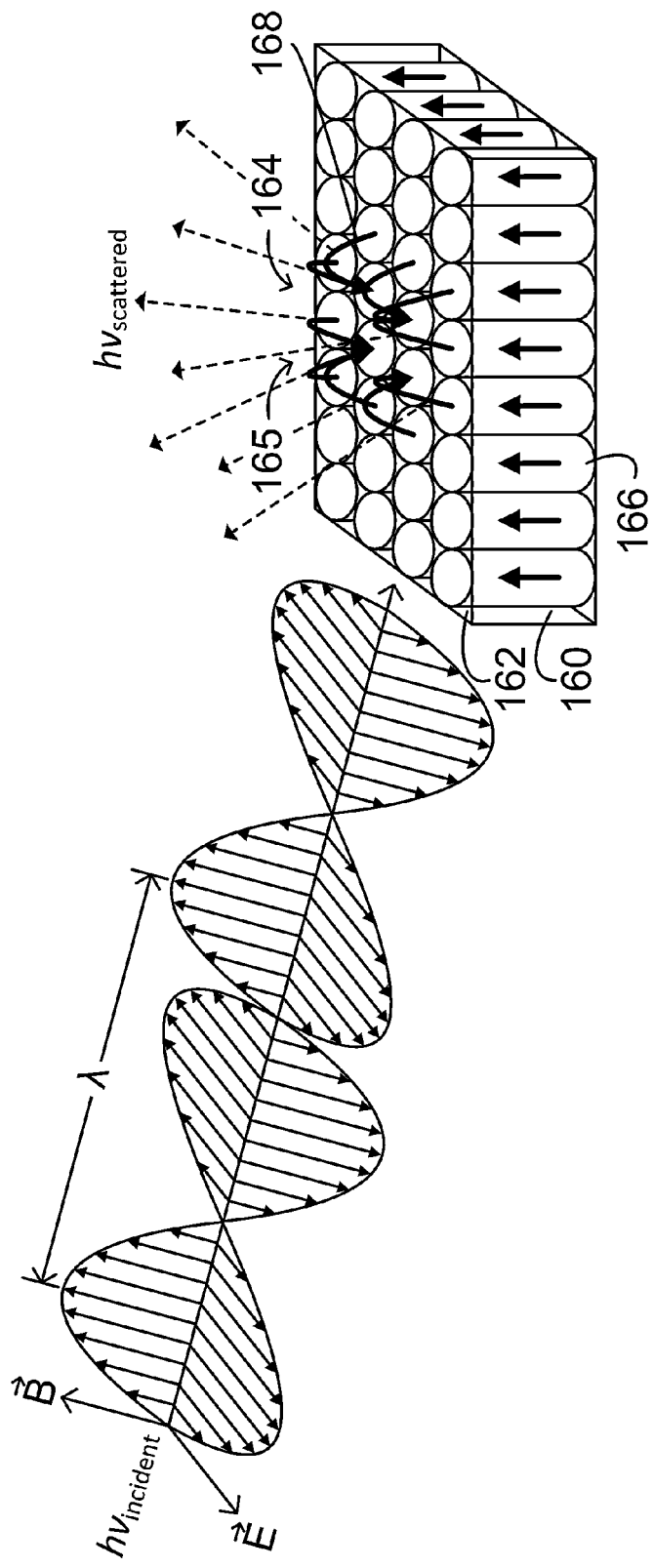

FIG. 6 provides a schematic illustrating photon scattering from a magnetic anomaly of a portion of an article according to one or more aspects.

DESCRIPTION

Before some particular embodiments are described and/or illustrated in greater detail, it should be understood by persons having ordinary skill in the art that the particular embodiments described and/or illustrated herein do not limit the concepts provided herein, as features in such particular embodiments may vary. It should likewise be understood that a particular embodiment described and/or illustrated herein has features that may be readily separated from the particular embodiment and optionally combined with or substituted for features in any of several other embodiments described and/or illustrated herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," and "down," or other similar terms such as "upper," "lower," "aft," "fore," "vertical," "horizontal," "proximal," and "distal," or the like, are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise.

Unless defined otherwise, all technical and scientific terms used herein have the same meaning as commonly understood by persons having ordinary skill in the art.

An article may be inspected for features, including defects that might degrade the performance of the article or a system including the article. For example, a hard disk for a hard disk drive may be fabricated on a production line and inspected for defects that might degrade the performance of the disk or the hard disk drive. Provided herein are apparatuses and methods for inspecting articles for features, including detecting, mapping, and/or distinguishing features of articles, which features include, but are not limited to, surface features and magnetic features.

With respect to articles that may be inspected with apparatuses and methods provided herein, such articles include any article of manufacture or a workpiece thereof in any stage of manufacture having one or more surfaces (e.g., one or more optically smooth surfaces), examples of which include, but are not limited to, semiconductor wafers, magnetic recording media (e.g., hard disks for hard disk drives), and workpieces thereof in any stage of manufacture. Such articles may be inspected for features such as surface features, including surface and/or subsurface defects that might degrade the performance of the article, which surface and/or subsurface defects include particle and stain contamination, as well as defects including scratches and voids. Alternatively or additionally, such articles may be inspected for features such as magnetic features, including magnetic anomalies that might degrade the performance of the article. As such, it is important to inspect articles with apparatuses and methods provided herein to correct manufacturing trends and to increase product quality.

FIG. 1 provides a basis from which to begin a description of features of the apparatuses and methods provided herein. In view of the foregoing, FIG. 1 provides a non-limiting schematic for detecting, mapping, and/or distinguishing features of articles illustrating an apparatus 100 including a photon emitter 110, an optical setup 120 including an optical component, a photon detector array 130, a computer or equivalent device 140, an optional stage 150 configured to support an article 160 and/or rotate an article 160 with respect to the photon emitter 110, and a features map 170 of the article 160. As such, FIG. 1 provides a basis from which to begin a description of photon emitters, optical components of the optical setup, photon detector arrays, etc. The apparatuses and methods provided herein are not limited to FIG. 1, as additional embodiments are provided herein, and additional embodiments may be realized by the features provided in more detail herein.

An apparatus may include a single photon emitter (e.g., photon emitter 110 of FIG. 1) to emit photons onto a surface of an article, such as the entire surface of the article or some predetermined portion of the surface of the article (e.g., for gradational rotation of the article for piecewise inspection, if desired). Alternatively, the apparatus may include a number of photon emitters (e.g., arranged at regular intervals around the optional stage 150 and/or the article 160 of FIG. 1) to individually emit photons onto the surface of the article, such as the entire surface of the article or some predetermined portion of the surface of the article, at different times and/or at the same time in any collection of photon emitters. In some non-limiting embodiments, for example, the apparatus may include at least 1, 2, 3, 4, 5, 6, 7, 8, 9, or 10 photon emitter(s). In some non-limiting embodiments, for example, the apparatus may include no more than 10, 9, 8, 7, 6, 5, 4, 3, 2, or 1 photon emitter(s). Combinations of the foregoing may also be used to describe the number of photon emitters of the apparatus. In some non-limiting embodiments, for example, the apparatus may include at least 2 photon emitters and no more than 10 photon emitters (e.g., between 2 and 10 photon emitters), such as at least 2 photon emitters and no more than 6 photon emitters (e.g., between 2 and 6 photon emitters), including at least 2 photon emitters and no more than 4 photon emitters (e.g., between 2 and 4 photon emitters). Each photon emitter of a number of photon emitters may be the same or different, or some combination thereof (e.g., at least 2 of the same photon emitter, with the remainder of photon emitters being different; at least 4 of the same photon emitter, with the remainder of photon emitters being different; etc.). In some non-limiting embodiments, for example, the apparatus may include at least two different photon emitters, wherein the two different photon emitters are each separately configured to emit photons onto a surface of an article, such as the entire surface of the article or some predetermined portion of the surface of the article.

Whether the apparatus includes a single photon emitter or a number of photon emitters, each photon emitter may emit photons onto a surface of an article at one or more distances and/or angles optimized for one or more types of features, which types of features are described in more detail herein. One angle may be equal to the glancing angle, which is the complement of the angle of incidence, and which angle of incidence is the angle between a ray including the emitted photons incident on the surface of the article and the normal (e.g., a line or vector perpendicular to the surface of the article) at the point at which the ray is incident. The glancing angle may also be described as an altitudinal angle or the smallest angle between a ray including the emitted photons incident on the surface of the article and the surface at the point at which the ray is incident.

FIGS. 2A and 2B provide a number of rays including emitted photons or $hv_{incident}$ incident on a surface 162 of an article 160, or a portion thereof, that form a glancing angle with the surface 162. FIG. 2A further provides a number of rays including reflected photons or $hv_{reflected}$ that form an angle of reflection with the normal to the surface, which angle of reflection is equal in magnitude to the angle of incidence. FIG. 2A even further provides a number of rays including scattered photons or $hv_{scattered}$ from a feature 164 (e.g., surface feature) on the surface 162 of the article 160, which rays including scattered photons form various scatter angles. Like FIG. 2A, FIG. 2B also provides a number of rays including scattered photons or $hv_{scattered}$ forming various scatter angles; however, the feature 164 from which the scattered photons are scattered is a magnetic feature represented by an example magnetic field line of a number of magnetic field lines.

A photon emitter may emit photons at a glancing angle ranging from 0° to 90°, inclusive, wherein a glancing angle of 0° represents the photon emitter emitting photons onto the surface of the article from a side of the article, and wherein a glancing angle of 90° represents the photon emitter emitting photons onto the surface of the article from directly above the article. In some non-limiting embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some non-limiting embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, 5°, or 0°. Combinations of the foregoing may also be used to describe the glancing angle at which a photon emitter may emit photons onto a surface of an article. In some non-limiting embodiments, for example, a photon emitter may emit photons onto a surface of an article such that the glancing angle is at least a 0° and no more than 90° (i.e., between 0° and 90°), such as at least 0° and no more than 45° (i.e., between 0° and 45°), including at least 45° and no more than 90° (i.e., between 45° and 90°).

A photon emitter may emit photons onto a surface of an article, such as the entire surface or some predetermined portion of the surface (e.g., for gradational rotation of the article for piecewise inspection, if desired). The photon emitter may further emit photons onto the entire surface of the article or some predetermined portion of the surface such that the entire surface or the predetermined portion of the surface is uniformly or homogenously illuminated. Uniformly illuminating the entire surface of the article or some predetermined portion of the surface includes, but is not limited to, subjecting the entire surface of the article or some predetermined portion of the surface of the article to the same or about the same quantity of photons per unit time (e.g., photon flux), the same or about the same photon energy per unit time (e.g., photon power), and/or the same or about the same photon power per unit area (e.g., photon power density or photon flux density). In radiometric terms, uniformly illuminating includes, but is not limited to, subjecting the entire surface of the article or some predetermined portion of the surface of the article to the same or about the same quantity of light per unit time, the same or about the same radiant energy per unit time (e.g., radiant power or radiant flux), and/or the same or about the same radiant power per unit area (e.g., irradiance or radiant flux density).

With the appreciation that photons are the elementary particles of electromagnetic radiation or light, a photon emitter or a light source may provide light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. A photon emitter or a light source may be used in conjunction with one or more optical components of an optical setup to provide light having any of the foregoing qualities. Wavelength filters, for example, may be used in conjunction with a photon emitter or a light source to provide light including a relatively wide range of wavelengths or frequencies, a relatively narrow range of wavelengths or frequencies, or a particular wavelength or frequency. Polarization filters, for example, may also be used in conjunction with a photon emitter or a light source to provide light of a desired polarization including polarized light, partially polarized light, or nonpolarized light. In some embodiments, for example, a photon emitter may provide photons of a relatively narrow range of wavelengths or a certain wavelength, the longer the wavelength(s) for which narrow range of wavelengths or certain wavelength the better the scattering of photons from surface features and/or magnetic features.

In view of the foregoing, a photon emitter or light source may include a lamp such as a flash lamp, including a high-speed flash lamp, configured to minimize vibration while detecting photons scattered from features of an article with a photon detector array. In some non-limiting embodiments, for example, a photon emitter or light source may include a high-speed Xe flash lamp such as a 500 W Xe flash lamp to minimize vibration while detecting photons scattered from features of an article with a photon detector array.

Also in view of the foregoing, a photon emitter or light source may include a collimated light source such as a laser, including a combination of lasers, configured to emit photons onto a surface of an article at one or more angles. In some non-limiting embodiments, for example, a combination of lasers may be provided to a laser beam shaper such that the combination of lasers emits photons onto a surface of an article at one angle. In some non-limiting embodiments, for example, a combination of lasers may be provided to a laser beam shaper such that the combination of lasers emits photons onto a surface of an article at multiple angles. In some non-limiting embodiments, for example, at least 2, 4, 6, 8, 10, 12, 14, 16, 18, 20, 22, 24, 26, 28, or 30 lasers, or even more than 30 lasers, may be provided to a laser beam shaper such that the combination of lasers emits photons onto a surface of an article at one or more angles. In some non-limiting embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some non-limiting embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may include a two-dimensional light source such as a combination of point light sources, including a linear combination or array, an arcuate combination or array, etc. of point light sources configured to emit photons onto a surface of an article. In some non-limiting embodiments, for example, a two-dimensional light source may include a combination of at least 10, 20, 40, 60, 80, 100, 110, 120, 140, 160, 180, or 200 point light sources, or even more than 200 point sources. In some non-limiting embodiments, for example, a two-dimensional light source may include a combination of no more than 200, 180, 160, 140, 120, 100, 80, 60, 40, 20, or 10 point light sources. Combinations of the foregoing may also be used to describe two-dimensional light sources including combinations of point light sources. In some non-limiting embodiments, for example, a two-dimensional light source may include a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be combined in rows and columns of a two-dimensional array, including linearly combined to form a two-dimensional light source such as a strip light. Such point light sources may be arcuately combined to form a two-dimensional light source such as a ring light. In some non-limiting embodiments, for example, a photon emitter or light source may include a two-dimensional light source including at least 60 point light sources, such as a ring light including at least 60 point light sources, optionally a ring light including at least 60 light-emitting diodes ("LEDs"), and further optionally a ring light including at least 100 LEDs. A two-dimensional light source including LEDs may include white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

The apparatus may further include a rotatable stage (e.g., rotatable stage 150 of FIG. 1) configured to gradationally rotate or continuously rotate an article through a number of rotational angles with respect to a photon emitter. Because some surface features differentially scatter photons under different rotational angles, for example, on account of their faceted surfaces, rotating an article through a number of rotational angles allows for such surface features to be detected, mapped, and/or distinguished. And, surprisingly, because magnetic features scatter photons orthogonally incident upon the magnetic features or certain magnetic field lines thereof, rotating an article through a number of rotational angles allows for such magnetic features to be detected, mapped, and/or distinguished. With respect to gradational rotation, an article may be sequentially rotated on the rotatable stage through a number of rotational angles, and the photon emitter may sequentially (or continuously) emit photons onto the surface of the article at each successive rotational angle. With respect to continuous rotation, an article may be continuously rotated on the rotatable stage through a number of rotational angles, and the photon emitter may continuously emit photons onto the surface of the article. Whether under gradational rotation or continuous rotation, photons scattered from the article's features at the number of rotational angles may be subsequently detected by the photon detector array (e.g., photon detector array 130 of FIG. 1). A features map (e.g., features map 170 of FIG. 1), or the information sufficient to produce such a features map, for each of the number of rotational angles may provide a set of differential features maps (e.g., 170A, 170B, 170C . . . 170n, wherein the index n indicates the $n^{th}$ features map from the $n^{th}$ rotational angle) that may be used to detect, map, and/or distinguish surface features and/or magnetic features that differentially scatter photons under different rotational angles. One or more composite features maps (e.g., one or more composite surface features maps, one or more composite magnetic features maps, or one or more composite surface features and magnetic features maps) may be generated from the differential features maps, or the information sufficient to produce such differential features maps, providing one or more composite features maps from any of a number of rotational angles, including all possible rotational angles.

The apparatus may further include an optical setup (e.g., optical setup 120 of FIG. 1 including one or more optical components), which optical setup may manipulate photons emitted from one or more photon emitters, photons reflected from a surface of an article, and/or photons scattered from features of an article. With the appreciation that photons are the elementary particles of electromagnetic radiation or light, the optical setup may manipulate light emitted from one or more photon emitters, light reflected from a surface of an article, and/or light scattered from features of an article. The optical setup up may include any of a number of optical components positioned before the article such that the optical components may be used to manipulate photons emitted from one or more photon emitters before uniformly or homogenously illuminating the entire surface or the predetermined portion of the surface of the article. Alternatively or additionally, the optical setup up may include any of a number of optical components positioned after the article such that the optical components may be used to manipulate photons reflected from the surface of the article or scattered from features of the article. Alternatively or additionally, an optical component including the article (e.g., article 160 of FIG. 1) may be used to manipulate (e.g., reflect) photons. The forgoing optical components may include, but are not limited to, optical components such as lenses, filters, gratings, and mirrors, which mirrors include articles having optically smooth surfaces.

With respect to optical components such as lenses, the optical setup may include a single lens or a number of lenses, including, but not limited to, a combination of a lens coupled to a photon detector array (e.g., the lens of the optical setup 120 coupled to the photon detector array 130 of FIG. 1) configured for collecting and detecting photons scattered from features of articles. The lens coupled to the photon detector array may have an entrance pupil and an exit pupil, and additional optical components such as lenses (e.g., lenses in addition to the lens coupled to the photon detector array), filters, gratings, and mirrors, may be positioned in any combination of one or more optical components at or near the entrance pupil of the lens coupled to the photon detector array, at or near the exit pupil of the lens coupled to the photon detector array (i.e., in-between the exit pupil of the lens and the photon detector array), or some combination thereof to manipulate photons scattered from features of articles. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the position of features of articles, reduces distortion of features of articles, enables quantitative analysis of photons scattered from features of articles, which quantitative analysis includes integration of photon scattering intensity distribution for size determination of features of articles.

With respect to optical components such as filters, the optical setup may include a filter or a number of filters including, but not limited to, one or more wavelength filters, band-pass filters, polarization filters, coherence filters, periodic array-tuned filters, and phase filters. As described herein, when one or more of such filters is positioned before an article to manipulate photons emitted from a photon emitter, photons/light having any of a number of different qualities may be provided to a surface of the article. When one or more of such filters is positioned after an article to manipulate photons scattered from features of the article, the one or more filters may be used for distinguishing features of the article. For example, a wavelength filter may be used to distinguish features that differentially scatter photons with respect to wavelength; a polarization filter may be used to distinguish features that differentially scatter photons with respect to polarization; a coherence filter may be used to distinguish features that differentially scatter photons with respect to coherence; and a phase filter or waveplate may be used to distinguish features that differentially scatter photons with respect to phase. In some non-limiting embodiments, for example, an optical component such as a filter may be positioned at or near the entrance pupil of a lens (e.g., telecentric lens) coupled to a photon detector array. In some non-limiting embodiments, for example, an optical component such as a filter may be positioned at or near the exit pupil of a lens (e.g., telecentric lens) coupled to a photon detector array.

With respect to optical components including reflective surfaces such as mirrors, the optical setup may include one or more mirrors of any curvature including, but not limited to, one or more mirrors selected from optical-grade mirrors and one-way mirrors, including articles including optically smooth surfaces. The one or more mirrors may be positioned about an apparatus to manipulate photons emitted from one or more photon emitters, reflected from a surface of an article, scattered from features of an article, or combinations thereof. As such, the one or more mirrors may be positioned in a light path before an article (e.g., a one-way mirror between a photon emitter and the article); in the light path after an article; or in combinations thereof. In some non-limiting embodiments, for example, one or more mirrors may be used to redirect photons reflected off a surface of an article back onto the surface of the article, thereby recycling photons that would otherwise be lost to the environment.

The apparatus may further include a single photon detector array (e.g., photon detector array 130 of FIG. 1) including a number of photon detectors to detect photons scattered from features of articles. Alternatively, the apparatus may further include a number of photon detector arrays, each including a number of photon detectors. In some non-limiting embodiments, for example, the apparatus may include at least 1, 2, 3, 4, 5, 6, 7, 8, 9, or 10 photon detector array(s). In some non-limiting embodiments, for example, the apparatus may include no more than 10, 9, 8, 7, 6, 5, 4, 3, 2, or 1 photon detector array(s). Combinations of the foregoing may also be used to describe the number of photon detector arrays of the apparatus. In some non-limiting embodiments, for example, the apparatus may include at least 1 photon detector array and no more than 10 photon detector arrays (e.g., between 1 and 10 photon detector arrays), such as at least 2 photon detector arrays and no more than 5 photon detector arrays (e.g., between 2 and 5 photon detector arrays). Each photon detector array of a number of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus includes a single photon detector array or a number of photon detector arrays, each photon detector array may be oriented to detect photons scattered from features of an article at one or more distances and/or angles for an optimum acceptance of the scattered photons (e.g., maximum acceptance of the scattered photons with minimum background noise, including noise from reflected photons) from one or more types of features, which types of features are described in more detail herein. Likewise, a lens-and-photon-detector-array combination may be oriented to collect and detect photons scattered from features of an article at one or more distances and/or angles for an optimum acceptance of the scattered photons from one or more types of features. One angle may be the angle between a ray including the center line axis of the lens and/or the photon detector array extended to the surface of the article and the normal (e.g., a line or vector perpendicular to the surface of the article) at the point at which the ray is extended. The angle, optionally in combination with an aperture that may be optimally sized for maximum acceptance of the scattered photons with minimum background noise, including noise from reflected photons, or optionally in combination with an aperture that may be variably sized, such as more widely sized or more narrowly sized to respectively accept a wider range or narrower range of the scattered photons, may be oriented to allow for acceptance of the scattered photons having a number of scatter angles, which scattered photons may be scattered from one or more types of features. A scatter angle may be different than the angle of reflection, which angle of reflection is equal in magnitude to the angle of incidence as described herein. FIG. 2A provides a number of rays including photons scattered from a feature 164 on a surface 162 of an article 160, which rays represent various scatter angles.

In view of the foregoing, the angle at which a photon detector array or a lens-and-photon-detector-array combination may be oriented ranges from 0° to 90°, inclusive, wherein an angle of 0° represents orientation of the photon detector array or the lens-and-photon-detector-array combination directly above the article, and wherein an angle of 90° represents orientation of the photon detector array or the lens-and-photon-detector-array combination at a side of an article. In some non-limiting embodiments, for example, a photon detector array or a lens-and-photon-detector-array combination may be oriented at an angle of at least 0°, 5°, 10°, 15°, 20°, 25°, 30°, 35°, 40°, 45°, 50°, 55°, 60°, 65°, 70°, 75°, 80°, 85°, or 90°. In some non-limiting embodiments, for example, a photon detector array or a lens-and-photon-detector-array combination may be oriented at an angle of no more than 90°, 85°, 80°, 75°, 70°, 65°, 60°, 55°, 50°, 45°, 40°, 35°, 30°, 25°, 20°, 15°, 10°, or 5°, or 0°. Combinations of the foregoing may also be used to describe the angle at which the photon detector array or the lens-and-photon-detector-array combination may be oriented. In some non-limiting embodiments, for example, a photon detector array or a lens-and-photon-detector-array combination may be oriented at an angle of at least a 0° and no more than a 90° (i.e., between 0° and 90°), such as least 0° and no more than 45° (i.e., between 0° and 45°) or at least 45° and no more than 90° (i.e., between 45° and 90°).

The photon detector array, optionally in combination with a lens (e.g., telecentric lens), may detect photons scattered from features of an article, such as the entire surface of the article or some predetermined portion of the surface of the article. The photon detector array, optionally in combination with a lens (e.g., telecentric lens), may detect photons scattered from features of an article, such as the entire surface of the article or some predetermined portion of the surface of the article, while oriented at a distance and/or an angle for an optimum acceptance of the scattered photons (e.g., maximum acceptance of photons with minimum background noise, including noise from reflected photons) from one or more types of features. As provided herein, the angle for an optimum acceptance of the scattered photons from one or more types of features may allow for acceptance of scattered photons respectively having a number of scatter angles, which scattered photons may respectively be scattered from one or more types of features.

With the appreciation that photons are the elementary particles of electromagnetic radiation or light, a photon detector array or a light detector array may detect light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As provided herein, a photon detector array or a light detector array may be used in conjunction with one or more optical components of an optical setup to detect light having any of the foregoing qualities.

The photon detector array may include a number of pixel sensors, which pixel sensors, in turn, may each include a photon detector (e.g., a photodiode) coupled to a circuit including a transistor configured for amplification. Features of a photon detector array including such pixel sensors include, but are not limited to, low temperature operation (e.g., down to −40° C.), low electron noise (e.g., 2-10 e⁻ RMS; 1 e⁻ RMS; <1 e⁻ RMS; etc.), wide dynamic range (e.g., 30,000:1, 8,500:1; 3,000:1; etc.), and/or decreased photon/light collection time. A photon detector array may include a large number of pixel sensors (e.g., ≥1,000,000 or ≥1M pixel sensors) arranged in rows and columns of a two-dimensional array, wherein each pixel sensor includes a photon detector coupled to an amplifier. In some non-limiting embodiments, for example, a photon detector array may include at least 1M, 2M, 3M, 4M, 5M, 6M, 7M, 8M, 9M, 10M, or more, pixel sensors arranged in rows and columns of a two-dimensional array. In some non-limiting embodiments, for example, a photon detector array may include no more than 10M, 9M, 8M, 7M, 6M, 5M, 4M, 3M, 2M, or 1M, pixel sensors arranged in rows and columns of a two-dimensional array. Combinations of the foregoing may also be used to describe the number of pixel sensors in a photon detector array. In some non-limiting embodiments, for example, a photon detector array may include at least 1M and no more than 10M (e.g., between 1M and 10M) pixel sensors arranged in rows and columns of a two-dimensional array, such as at least 1M and no more than 8M (e.g., between 1M and 8M) pixel sensors, including at least 1M and no more than 6M (e.g., between 1M and 6M) pixel sensors, further including at least 2M and no more than 6M (e.g., between 2M and 6M) pixel sensors, and even further including at least 2M and no more than 5M (e.g., between 2M and 5M) pixel sensors.

Due to small angle scattering (e.g., $4\pi$ scattering) features may appear much larger in size enabling pixel sensors larger the than features to be used. In some non-limiting embodiments, for example, a photon detector array may include micrometer-sized (i.e., admits of μm units as measured) pixel sensors at least 1 μm, 2 μm, 3 μm, 4 μm, 5 μm, 6 μm, 7 μm, 8 μm, 9 μm, or 10 μm in their smallest dimension. In some non-limiting embodiments, for example, a photon detector array may include micrometer-sized pixel sensors no more than 10 μm, 9 μm, 8 μm, 7 μm, 6 μm, 5 μm, 4 μm, 3 μm, 2 μm, or 1 μm in their smallest dimension. Combinations of the foregoing may also be used to describe dimensions of micrometer-sized pixel sensors in photon detector arrays. In some non-limiting embodiments, for example, a photon detector array may include micrometer-sized pixel sensors at least 1 μm and no more than 10 μm (e.g., between 1 μm and 10 μm) in their smallest dimension, such as at least 1 μm and no more than 7 μm (e.g., between 1 μm and 7 μm), including at least 4 μm and no more than 10 μm (e.g., between 4 μm and 10 μm), and further including at least 4 μm and no more than 7 μm (e.g., between 4 μm and 7 μm). Such micrometer-sized pixel sensors may be used in the apparatus for detecting, mapping, and/or distinguishing features of articles, wherein the features are more than 100 times smaller than the micrometer-sized pixel sensors.

In view of the foregoing, the single photon detector array or the number of photon detector arrays may each include a complementary metal-oxide semiconductor ("CMOS") or a scientific complementary metal-oxide semiconductor ("sCMOS"), each of which may be optionally part of a CMOS camera or a sCMOS camera, respectively. Alternatively, the single photon detector array or the number of photon detector arrays may each include a charge-coupled device ("CCD"), which may optionally be part of CCD camera. While a CCD-based photon detector array might have a slower recording speed than a CMOS-based or sCMOS-based photon detector array, a CCD-based photon detector array may be desirable in applications requiring less electronic and/or image noise. A CCD-based photon detector array, including an electron-multiplying CCD ("EMCCD"), may also be desirable in certain applications having low-light conditions. Furthermore, a number of photon detector arrays is not limited to combinations of either CMOS/sCMOS-based photon detector arrays or CCD-based photon-detector arrays, as a number of photon detector arrays may include a combination of any of a number of CMOS/sCMOS-based photon detector arrays and CCD-based photon-detector arrays in applications that benefit from employing each type of technology. In some non-limiting embodiments, for example, a CMOS/sCMOS-based photon detector array may be used to detect photons scattered from features of articles in certain applications having sufficient light for the CMOS/sCMOS-based photon detector array, while a CCD/EMCCD-based photon detector array may be used to detect photons scattered from features of articles in certain applications having too little light for the CMOS/sCMOS-based photon detector array.

FIG. 3 provides a schematic for detection of features of an article, illustrating a close-up, cross-sectional view of an apparatus including an optical setup and a photon detector array as provided herein. As shown, article 160 includes a surface 162 and one or more features such as feature 164 (e.g., surface feature, magnetic feature, etc.). Photons may be scattered by the features and collected and detected by a combination including a lens coupled to a photon detector array 130, which combination may be positioned at a distance and/or an angle for an optimum acceptance of the scattered photons (e.g., maximum acceptance of photons with minimum background noise, including noise from reflected photons) from one or more types of features. The optical setup, which may include a telecentric lens (e.g., the lens of the optical setup 120 of FIG. 1), may collect and focus the photons scattered from one or more features onto one or more pixel sensors 132 of photon detector array 130, which one or more pixel sensors may each include a photon detector coupled to an amplifier (e.g., CMOS/sCMOS-based photon detector array; EMCCD-based photon detector array; etc.). The one or more pixel sensors 132, each of which may correspond to a particular, fixed area of an article's surface and a pixel in a features map of the article, may provide one or more signals to a computer or equivalent device for mapping an article's features or otherwise determining the position of one or more features of the article.

Depending upon factors that may include the type of article, the type of surface features (e.g., particle, stain, scratch, void, etc.), the type of magnetic features, and the like, it may be desirable at times to increase detection time of a single photon detector array or a number of photon detector arrays to detect more photons for detecting, mapping, and/or distinguishing features of articles. In some non-limiting embodiments, for example, detection time of a single photon detector array or a number of photon detector arrays may be increased to detect more photons. In such embodiments, a CCD-based photon detector array, including an electron-multiplying EMCCD may be used to further detect more photons. Alternately or additionally, it may be desirable to increase the number of photons (e.g., photon energy) emitted from a single photon emitter or a number of photon emitters to provide an increase in photons scattered for detecting, mapping, and/or distinguishing features of articles. Such an increase in photon energy may be with respect to unit time for increased photon power, or with respect to unit area for increased photon flux density. Alternately to one or both of increasing the photon energy or detection time, or in addition to increasing the photon energy and detection time, it may be desirable at times to minimize background noise including stray light from one or more photon emitters, reflected light from the surface of the article, background light, and/or background fluorescent radiation.

The apparatus may further include one or more computers or equivalent devices (e.g., devices that include primary and/or secondary memory and one or more processing elements operable to carry out arithmetic and logical operations), including, but not limited to, servers, workstations, desktop computers, nettops, laptops, netbooks, and mobile devices such as tablets and smartphones, which computers or equivalent devices may contain graphics processing units ("GPU's), application-specific integrated circuits ("ASIC"s), field-programmable gate arrays ("FPGA"s), etc. The computers or equivalent devices may include a computer-readable storage medium for instructions making the apparatus operable to, but not limited to, convey each article to the apparatus for inspection; position each article for inspection, optionally including gradational or continuous rotation of the article with respect to the photon emitter(s); hold or otherwise maintain the position of each article for inspection; insert optical components into the optical setup, for example, using a mechanical actuator; position optical components for inspection; adjust optical components (e.g., focus lenses) and/or tune optical components (e.g., piezoelectric-based wavelength filters; piezoelectric-based polarization filters; etc.) for inspection; remove optical components from the optical setup; move each photon emitter into position for inspection, wherein the position for inspection may include a photon emitter-article distance and/or angle (e.g., glancing angle) optimized for one or more types of features; switch each photon emitter on and off, or otherwise between modes for emitting photons and not emitting photons; move each photon detector array into position for inspection, wherein the position for inspection may include a photon detector array-article distance and/or angle (e.g., scatter angle) optimized for one or more types of features; switch each photon detector array on and off, or otherwise between modes for detecting photons and not detecting photons; synchronize each photon emitter with each photon detector in accordance with a photon emission-photon detection scheme; process photon-detector-array signals or derivative signals thereof corresponding to scattered photons, optionally including pixel interpolation for better accuracy (e.g., 10× better than pixel size) with respect to the position of features; map or otherwise determine the position of features of articles from photon-detector-array signals or derivative signals thereof; quantitatively and/or qualitatively characterize features of articles; catalog features of articles; and determine trends with respect to features of articles.

The one or more computers or equivalent devices may generate a features map such as a surface features map using photon-detector-array signals or derivative signals thereof corresponding to photons scattered from one or more types of surface features. FIG. 4A provides an image of such a surface features map, FIG. 4B further provides a close-up image of such a surface features map (e.g., a close-up image of the surface features map of FIG. 4A), and FIG. 4C (top) even further provides a closer, close-up image of such a surface features map (e.g., a close-up image of the surface features map of FIG. 4B), wherein the close-up image of FIG. 4C is centered about a single surface feature (e.g., feature 164 of FIG. 3). The one or more computers or equivalent devices may subsequently use pixel interpolation for further mapping surface features such as the surface feature provided in FIG. 4D (top). As evidenced by inspection of the close-up images of the surface feature in FIGS. 4C (top) and 4D (top), pixel interpolation increases pixel resolution for the surface features map to which it is applied, importantly without an increase in pixel sensors in the photon detector array. Such pixel interpolation may further increase resolution for photon scattering intensity distributions as evidenced by inspection of the photon scattering intensity distributions in FIGS. 4C (bottom) and 4D (bottom) respectively for the surface feature of FIGS. 4C (top) and 4D (bottom).

The one or more computers or equivalent devices may generate a features map such as a magnetic features map using photon-detector-array signals or derivative signals thereof corresponding to photons scattered from one or more types of magnetic features. FIG. 5B provides an image of such a magnetic features map, wherein photons scattered by magnetic features across an inner diameter band and an outer diameter band of an annular or disk-shaped article (e.g., hard disk for a hard disk drive) indicates correctly written magnetic information (e.g., by a disk certifier for hard disk certification), and wherein a lack of photons scattered across a middle band of the article indicates one or more magnetic anomalies, including, but not limited to, magnetic defects and incorrectly written magnetic information. FIG. 5C provides magnetic force microscopy ("MFM") images for the inner diameter band, the middle band, and the outer diameter band overlaying the image of the magnetic features map of FIG. 5B. The MFM images of FIG. 5C further provide evidence that the inner diameter band and the outer diameter band of the article includes correctly written magnetic information (e.g., by a disk certifier for hard disk certification), while the middle band of the article includes magnetic anomalies.

It was surprisingly discovered that articles including magnetic features such as the article of FIG. 5B scatter photons orthogonally incident upon the magnetic features or certain magnetic field lines thereof. FIG. 2B provides a schematic illustrating this surprising discovery, in which photons in one of a number of rays or $hv_{incident}$ emitted onto a surface 162 of an article 160 are scattered in a number of rays or $hv_{scattered}$ by features 164 such as magnetic features 164 including magnetic domains 166, to which magnetic features 164 or certain magnetic field lines 168 thereof the photons in the one of the number of rays or $hv_{incident}$ are orthogonal. Without being bound by theory, the photons in the one of the number of rays emitted onto the surface of the article interact with the magnetic field lines of magnetic features, thereby allowing the magnetic features to scatter photons. Further without being bound by theory, tightly packed or dense arrangements of magnetic domains and magnetic transitions between them in magnetic recording media, including, but not limited to, longitudinal magnetic recording media ("LMR"), perpendicular magnetic recording media ("PMR"), heat-assisted magnetic recording media ("HAMR"), discrete track recording media ("DTR"), and bit-patterned media ("BPM"), makes possible or enhances the scattering of photons by magnetic features.

Turning back to FIG. 5B and without being bound by theory, the lack of photons scattered across the middle band of the article may be explained by reference to FIG. 5A, which provides a schematic illustrating a lack of photon scattering from a magnetic anomaly 165 about a surface 162 of a portion of an article 160. As illustrated in FIG. 5A, magnetic domains 166 may be arranged in tracks by like polarizations (e.g., "↓" and "↑") such as tracks magnetically written by a disk certifier for hard disk certification. Magnetic transitions between the magnetic domains 166 are illustrated in FIG. 5A by magnetic field lines 168 forming magnetic features 164, which magnetic features 164 scatter photons as provided herein. However, since the magnetic anomaly 165 does not share a magnetic transition with one or more magnetic domains 166, the magnetic anomaly 165 does not form a magnetic feature 164, and the magnetic anomaly 165 does not scatter photons. In this non-limiting example, the magnetic anomaly may be an artifact of article fabrication such as a magnetic defect resulting from faulty magnetic stack construction in the region of the article corresponding to the magnetic anomaly. Alternatively or in addition, the magnetic anomaly may be incorrectly written magnetic information such as incorrectly written magnetic information by a disk certifier for hard disk certification.

Turning to FIG. 6 and without being bound by theory, FIG. 6 provides a schematic illustrating photon scattering from a magnetic anomaly 165 about a surface 162 of a portion of an article 160. Magnetic domains (e.g., magnetic domains 166) of the article may be oriented in one polarization or an opposite polarization (e.g., "↓" or "↑") by DC magnetization of the article, for example, a hard disk for a hard disk drive. Ideally, DC magnetization of the article removes magnetic transitions between nearby magnetic domains encouraging magnetic field lines (e.g., magnetic field line 168) of the magnetic domains to instead close over and back under the article, for example, over and back under the inner and outer circumferences of the hard disk. However, weak or poorly constructed magnetic domains of the article may spontaneously change polarization after DC magnetization allowing for magnetic transitions between DC magnetized magnetic domains and the weak or poorly constructed magnetic domains. In other words, the weak or poorly constructed magnetic domains may spontaneously change polarization after DC magnetization allowing for magnetic field lines of nearby magnetic domains to close through the surface of the article and through the weak or poorly constructed magnetic domains instead of over and back under the article. On account of magnetic transitions between DC magnetized magnetic domains and the weak or poorly constructed magnetic domains, magnetic anomalies (e.g., magnetic anomaly 165) including the weak or poorly constructed magnetic domains scatter photons as described herein for magnetic features (e.g., magnetic feature 164).

Articles such as hard disks having servo patterns in servo sectors, including, but not limited to servo patterns corresponding to one or more servo sector fields selected from an automatic gain control ("AGC") field, a servo timing mark ("STM") field, a Gray-coded track number field, and a position error signal ("PES") burst pattern field may be inspected for detecting, mapping, and/or distinguishing magnetic features. In some non-limiting embodiments, for example, Gray-coded track number fields of hard disks, which fields include successive track numbers differing only in a single bit, may be inspected for magnetic anomalies. In such embodiments, magnetic features of the Gray-coded track number fields predictably vary in accordance with successive track numbers differing only in a single bit. Any magnetic features of the Gray-coded track number fields not in accordance with expected magnetic features may be considered magnetic anomalies.

Since FIG. 5A provides a schematic illustrating a lack of photon scattering from a magnetic anomaly and FIG. 6 provides a schematic illustrating photon scattering from a magnetic anomaly, it should be understood that magnetic anomalies of articles may present differently according to the scenario under which the articles are inspected. And while FIG. 5A and FIG. 6 present two such scenarios, it should be further understood that apparatuses and methods provided herein are not limited thereto.

The apparatus may be configured for detecting, mapping, and/or distinguishing features of articles, wherein the features are nanometer-sized (i.e., admits of nm units as measured) or smaller in their smallest dimension (e.g., length, width, height, or depth, depending on the feature), which features may be smaller than the wavelength of photons emitted from a photon emitter of the apparatus. However, the apparatus is not limited to features of articles that are nanometer-sized or smaller, as the apparatus may be configured for detecting, mapping, and/or distinguishing features of articles, wherein the features are micrometer-sized (i.e., admits of μm units as measured) or larger. In some non-limiting embodiments, for example, the apparatus may be configured for detecting, mapping, and/or distinguishing features of articles, wherein the features are smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as features of articles smaller than 9 Å, 8 Å, 7 Å, 6 Å, 5 Å, 4 Å, 3 Å, 2 Å, or 1 Å in their smallest dimension. In view of the foregoing, and in some non-limiting embodiments, for example, the apparatus may be configured for detecting, mapping, and/or distinguishing features of articles, wherein the features are between 0.1 nm and 1000 nm, such as between 0.1 nm and 500 nm, including between 0.1 nm and 250 nm, and further including between 0.1 nm and 100 nm, and even further including between 0.1 nm and 80 nm. Furthermore, the apparatus may be configured for detecting, mapping, and/or distinguishing features having a depth more than 1 nm, 2 nm, 3 nm, 4 nm, 5 nm, 6 nm, 7 nm, 8 nm, 9 nm, or 10 nm, or deeper, below an article's surface.

The apparatus may be configured for detecting, mapping, and/or distinguishing surface features of articles, including surface and/or subsurface defects including particle contamination in which the particles are nanometer-sized (i.e., admits of nm units as measured) or smaller in their smallest dimension (e.g., length, width, or height). In some non-limiting embodiments, for example, the apparatus may be configured for detecting, mapping, and/or distinguishing surface and/or subsurface particles smaller than 125 nm, such as smaller than 100 nm, including smaller than 80 nm, and further including smaller than 10 nm in their smallest dimension. Detecting, mapping, and/or distinguishing surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some non-limiting embodiments, for example, the apparatus may be configured for detecting, mapping, and/or distinguishing surface and/or subsurface particles as small as or smaller than 4 nm in height.

The apparatus may be configured for detecting, mapping, and/or distinguishing surface features of articles, including surface and/or subsurface defects including scratches (e.g., circumferential scratches) that are micrometer-sized (i.e., admits of μm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be configured for detecting, mapping, and/or distinguishing scratches from, for example, 1 μm to 1000 μm in length, which may be significantly longer than the wavelength of photons emitted from a photon emitter of the apparatus. In some non-limiting embodiments, for example, the apparatus may be configured for detecting, mapping, and/or distinguishing scratches smaller than 1000 μm, such as smaller than 500 μm, including smaller than 250 μm, further including smaller than 100 μm, and even further including smaller than 50 μm in scratch length. With respect to nanometer-sized scratches, the apparatus may be configured for detecting, mapping, and/or distinguishing scratches from, for example, 1 nm to 500 nm in scratch width. In some non-limiting embodiments, for example, the apparatus may be configured for detecting, mapping, and/or distinguishing scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be configured for detecting, mapping, and/or distinguishing angstrom-sized scratches with respect to scratch depth. In some non-limiting embodiments, for example, the apparatus may be configured for detecting, mapping, and/or distinguishing scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be configured for detecting, mapping, and/or distinguishing scratches smaller than 500 μm in length, smaller than 100 nm in width, and smaller than 50 Å in depth.

The apparatus may be operable to accurately and/or precisely map or otherwise determine the position of a feature (e.g., surface feature in FIGS. 4C [top] and 4D [top]) about an article, optionally using pixel interpolation. With respect to accuracy, the apparatus may be operable to map or otherwise determine the position of a feature about an article within a micrometer-sized (i.e., admits of μm units as measured) radius or better. In some non-limiting embodiments, for example, the apparatus may be operable to accurately map or otherwise determine the position of a feature about an article within a radius of 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, or 1 μm, or better. Combinations of the foregoing may also be used to describe the accuracy with which the apparatus may map or otherwise determine the position of a feature about an article. In some non-limiting embodiments, for example, the apparatus may be operable to accurately map or otherwise determine the position of a feature about an article within a radius ranging from 1 μm to 100 μm, such as from 1 μm to 50 μm, including from 1 μm to 30 μm, and further including from 5 μm to 10 μm.

In addition to accurately and/or precisely mapping or otherwise determining the position of a feature about an article, the apparatus may be operable to accurately and/or precisely determine the photon scattering intensity distribution (e.g., FIGS. 4C [bottom] and 4C [bottom]) of the feature about the article. Such a photon scattering intensity distribution may be used to characterize a feature about an article quantitatively and/or qualitatively, which, in turn, may be used for distinguishing features of articles.

With respect to quantitative characterization of a feature of an article, mathematical integration of a photon scattering intensity distribution provides the size (e.g., volume) of the feature of the article. Quantitative characterization of a feature of an article may further include a determination of feature position about the article as described herein. Quantitative characterization may even further include the total number of features per article, or the number of features per unit area per article (e.g., feature density), as well as the number of each type of feature per article. Such characterization information may be cataloged across a number of articles and be used to correct manufacturing trends should such features include defects (e.g., magnetic anomalies, surface defects, and/or subsurface defects) that might degrade the performance of the article.

With respect to qualitative characterization of a feature of an article such as a surface feature, qualitative characterization may include a determination whether the surface feature is a particle, a stain, a scratch, a void, etc., which determination may be effected by, but is not limited to, analysis of the feature's photon scattering intensity distribution. Qualitative characterization may further include chemical characterization of surface features known to differentially scatter photons such as, but not limited to, certain oxides, which may have faceted surfaces that differentially and/or directionally scatter photons depending upon rotational orientation to the photon emitter(s). Qualitative characterization may even further include distinguishing between surface features known to differentially scatter photons with respect to wavelength, polarization, coherence, and/or phase. A wavelength filter may be used to distinguish between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some non-limiting embodiments, for example, qualitative characterization of one or more surface features of an article may include contrasting photon-scattering information in the effective absence of one of the foregoing filters with photon-scattering information using one or more of the foregoing filters or contrasting a first surface features map produced in the effective absence of one of the foregoing filters with a second surface features map (or a number of surface features maps) produced using one or more of the foregoing filters. Along with quantitative characterization information, such qualitative characterization information may be cataloged across a number of articles and be used to correct manufacturing trends should features include defects (e.g., magnetic anomalies, surface defects, and/or subsurface defects) that might degrade the performance of the article.

The apparatus described herein may be configured to process or inspect articles at a rate greater than or commensurate with the rate at which the articles or workpieces thereof are produced. In some non-limiting embodiments, for example, the apparatus may be configured to process or inspect articles at a rate of at least 1, 2, 3, 4, 5, 6, 7, 8, 9, 10, 12, 14, 16, 18, or 20, or higher, article(s) per second, which rate may be commensurate with the rate at which the articles or workpieces thereof are produced. In some non-limiting embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some non-limiting embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, with a number of photon emitters arranged at regular intervals around an article, the article need not be rotated during processing or inspecting. As such, the apparatus may be configured to hold an article stationary while emitting photons onto the surface of the article.

As such, provided herein is an apparatus, comprising a photon emitter configured to emit photons onto a surface of an article; a photon detector array configured to receive photons scattered from the article; and a processing means operably connected to the photon detector array, wherein the apparatus is operable to detect magnetic anomalies among magnetic features of the article. In some embodiments, the apparatus further comprises a stage configured to rotate the article with respect to the photon emitter. In some embodiments, the photon emitter is further configured to emit photons orthogonally to magnetic field lines of the magnetic features. In some embodiments, the apparatus further comprises a telecentric lens operably connected to the photon detector array. In some embodiments, the processing means comprises a processor configured to execute arithmetic and logical operations on photon-detector-array signals or derivative signals thereof corresponding to the photons received by the photon detector array. In some embodiments, the processing means is operable to generate at least one magnetic features map of the article. In some embodiments, the apparatus is further operable to detect surface features about the surface of the article, and wherein the surface features are selected from a group consisting of particles, stains, scratches, and voids. In some embodiments, the processing means is operable to generate at least one surface features map of the article.

Also provided is an apparatus, comprising a photon emitting means configured to emit photons onto a surface of an article; a photon detector array configured to receive photons scattered from the surface of the article; and a processing means operably connected to the photon detector array, wherein the apparatus is operable to detect magnetic anomalies among magnetic features of the article. In some embodiments, the photon emitting means is configured to emit photons orthogonally to magnetic field lines of the magnetic features. In some embodiments, the photon emitting means comprises a photon emitter and a stage, wherein the stage is configured to rotate the article with respect to the photon emitter. In some embodiments, the apparatus further comprises a telecentric lens operably connected to the photon detector array. In some embodiments, the processing means comprises a processor configured to execute arithmetic and logical operations on photon-detector-array signals or derivative signals thereof corresponding to the photons received by the photon detector array. In some embodiments, the processing means is operable to generate at least one features map of the article, wherein the features of the features map comprise magnetic features, surface features, or a composite features map thereof.

Also provided is an apparatus, comprising a photon emitting means configured to emit photons, wherein the photons are scattered from magnetic features of an article; a photon detector array configured to receive scattered photons; and a processing means configured to differentiate the magnetic features from the scattered photons. In some embodiments, the photon emitting means is further configured to emit photons orthogonally to magnetic field lines of the magnetic features. In some embodiments, the photon emitting means comprises a photon emitter and a stage, wherein the stage is configured to rotate the article with respect to the photon emitter. In some embodiments, the apparatus further comprises a telecentric lens operably connected to the photon detector array. In some embodiments, the processing means comprises a processor configured to execute arithmetic and logical operations on photon-detector-array signals or derivative signals thereof corresponding to the photons received by the photon detector array. In some embodiments, the processing means is operable to generate at least one features map of the article, wherein the features of the features map comprise magnetic features, surface features, or a composite features map thereof.

Also provided is an apparatus, comprising a photon detector array configured to receive photons scattered from an article; and a processing means operably connected to the photon detector array, wherein the apparatus is operable to detect magnetic anomalies among magnetic features of the article. In some embodiments, the apparatus further comprises a photon emitter configured to emit photons onto the surface of the article. In some embodiments, the apparatus further comprises a stage configured to position the article with respect to the photon emitter such that the photons are emitted orthogonally to magnetic field lines of the magnetic features. In some embodiments, the apparatus further comprises a telecentric lens operably connected to the photon detector array. In some embodiments, the processing means comprises a processor configured to execute arithmetic and logical operations on photon-detector-array signals or derivative signals thereof corresponding to the photons received by the photon detector array. In some embodiments, the processing means is operable to generate at least one features map of the article, wherein the features of the features map comprise magnetic features, surface features, or a composite features map thereof.

While some particular embodiments have been described and/or illustrated herein, and while these particular embodiments have been described and/or illustrated in considerable detail, it is not the intention for these particular embodiments to limit the scope of the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts provided herein. The implementations provided herein and other implementations are within the scope of the following claims.

What is claimed is:

1. An apparatus, comprising:
   a photon emitter configured to emit photons onto a surface of an article;
   a photon detector array configured to receive photons scattered from magnetic features of the article,
   wherein the magnetic features are characterized by transitional magnetic field lines between magnetic domains of the article; and
   a processing means operably connected to the photon detector array,
   wherein the apparatus is operable to detect magnetic anomalies among the magnetic features by a lack of photons scattered from the magnetic anomalies.

2. The apparatus of claim 1, further comprising a stage configured to rotate the article with respect to the photon emitter.

3. The apparatus of claim 1, wherein the photon emitter is further configured to emit photons orthogonally to the transitional magnetic field lines.

4. The apparatus of claim 3, wherein the photon emitter is further configured to emit photons uniformly over the entire surface of the article, and wherein the photon emitter is a flash lamp configured to minimize vibration while the photon detector array receives photons scattered from the magnetic features.

5. The apparatus of claim 1, further comprising a telecentric lens operably connected to the photon detector array.

6. The apparatus of claim 5, wherein the photon detector array comprises a plurality of pixel sensors corresponding to particular, fixed areas of the surface of the article and particular pixels in a magnetic features map of the article.

7. The apparatus of claim 1,
wherein the processing means comprises a processor configured to execute arithmetic and logical operations on photon-detector-array signals or derivative signals thereof corresponding to the photons received by the photon detector array.

8. The apparatus of claim 1,
wherein the processing means is operable to generate at least one magnetic features map of the article.

9. The apparatus of claim 1,
wherein the apparatus is further operable to detect surface features about the surface of the article, and
wherein the surface features are selected from a group consisting of particles, stains, scratches, and voids.

10. The apparatus of claim 9,
wherein the processing means is operable to generate at least one surface features map of the article.

11. The apparatus of claim 1,
wherein the magnetic anomalies are magnetic defects resulting from faulty magnetic stack construction.

12. An apparatus, comprising:
a photon emitting means configured to emit photons,
   wherein the photons are scattered from magnetic features characterized by transitional magnetic field lines between magnetic domains of an article;
a photon detector array configured to receive scattered photons; and
a processing means configured to differentiate the magnetic features from magnetic anomalies by the scattered photons or a lack thereof.

13. The apparatus of claim 12,
wherein the photon emitting means is further configured to emit photons orthogonally to the transitional magnetic field lines.

14. The apparatus of claim 13,
wherein the photon emitting means comprises a photon emitter and a stage, and
wherein the stage is configured to rotate the article with respect to the photon emitter.

15. The apparatus of claim 13, further comprising
a telecentric lens operably connected to the photon detector array.

16. The apparatus of claim 13,
wherein the processing means is operable to generate at least one features map of the article, and
wherein the features of the features map comprise magnetic features, surface features, or a composite features map thereof.

17. An apparatus, comprising:
a photon detector array configured to receive photons scattered from magnetic features of an article; and
a processing means operably connected to the photon detector array,
   wherein the apparatus is operable to detect magnetic anomalies among the magnetic features by a lack of photons scattered from the magnetic anomalies.

18. The apparatus of claim 17, further comprising
a photon emitter configured to emit photons onto a surface of the article.

19. The apparatus of claim 18, further comprising
a stage configured to position the article with respect to the photon emitter such that the photons are emitted orthogonally to transitional magnetic field lines between magnetic domains of the article.

20. The apparatus of claim 17, further comprising
a telecentric lens operably connected to the photon detector array.

21. The apparatus of claim 17,
wherein the processing means is operable to generate at least one features map of the article, and
wherein the features of the features map comprise magnetic features, surface features, or a composite features map thereof.

* * * * *